United States Patent
Falsey

(10) Patent No.: US 6,562,007 B1
(45) Date of Patent: May 13, 2003

(54) ADJUSTABLE DOSAGE SYRINGE

(75) Inventor: Thomas A. Falsey, Overland Park, KS (US)

(73) Assignee: Bayer Healthcare LLC, Tarrytown, NY (US)

( * ) Notice: Subject to any disclaimer, the term of this patent is extended or adjusted under 35 U.S.C. 154(b) by 92 days.

(21) Appl. No.: 09/672,391

(22) Filed: Sep. 28, 2000

(51) Int. Cl.[7] ................................................ A61M 5/00
(52) U.S. Cl. ..................................................... 604/211
(58) Field of Search ........................... 604/208, 15, 18, 604/519, 518, 59, 186, 188, 207, 211, 221, 181, 187, 209, 210, 218, 220, 224, 225, 235

(56) References Cited

U.S. PATENT DOCUMENTS

| | | | |
|---|---|---|---|
| 2,856,925 A | 10/1958 | Helmer et al. | 128/218 |
| 3,563,240 A | 2/1971 | Silver | 128/234 |
| 4,275,729 A | 6/1981 | Silver et al. | 128/218 C |
| 5,308,340 A | * 5/1994 | Harris | 604/208 |
| 6,194,408 B1 | * 2/2001 | Kennedy | 514/241 |

* cited by examiner

Primary Examiner—Brian L. Casler
Assistant Examiner—Mark K. Han
(74) Attorney, Agent, or Firm—Susan M. Pellegrino

(57) ABSTRACT

Disclosed herein is a self-zeroing dosage syringe comprising: (a) a syringe barrel which forms a volume sufficient to contain a required dosage of a fluid, a discharge end at one end of the barrel length, a plunger receiving end at the opposite end of the barrel length, (b) said plunger is movably disposed within the barrel and has a length greater than the length of the barrel, and further has at a set of multiple closely spaced indentations disposed along the length thereof, and (c) a movable dosage selection ring which is disposed around the plunger and rotatable about the longitudinal axis of the plunger; characterized in that the dosage selection ring has (1) a sleeve disposed inside the barrel, (2) a calibration on the sleeve thereof for setting the desired dosage by turning the ring until the calibration for a desired dose is reached, (3) a means for engaging the ring with the plunger allowing it to be moved cooperatively with the plunger until the ring dead ends against the syringe barrel thereby releasing the desired dosage.

11 Claims, 5 Drawing Sheets

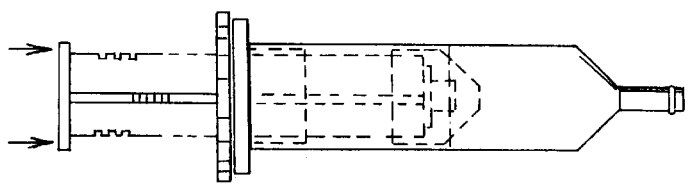
FIG. 7
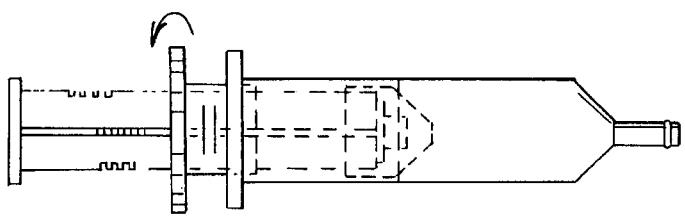
FIG. 6
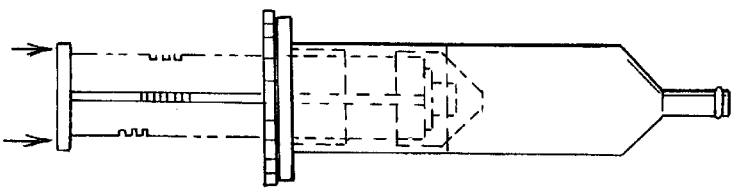
FIG. 5
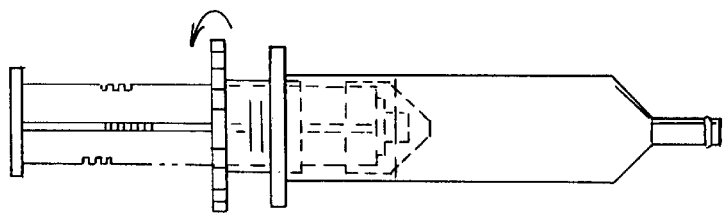
FIG. 4
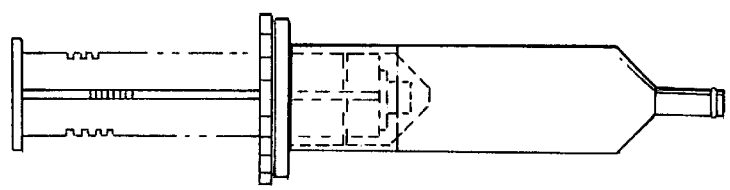
FIG. 3
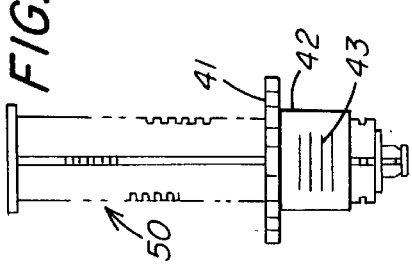
FIG. 2
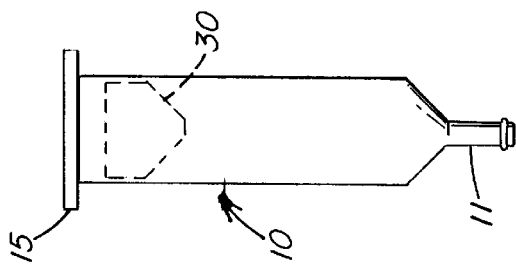

ADJUSTABLE DOSAGE SYRINGE

BACKGROUND OF THE INVENTION

1. Field of the Invention

The present invention relates to adjustable dosage syringes and more specifically to self-zeroing syringes that can be used to administer multiple doses by single loading of the syringe.

2. Brief Description of the Prior Art

Adjustable dosage syringes have been used in the art for either adjusting the dosage for a particular administration of the contents of the syringes and/or for delivering multiple dosages of the contents of the syringe in multiple separate injections. For example, in veterinary use, the dosage of a particular drug administered to an animal may vary considerably with the weight of an animal. Thus, when a herd of livestock is injected with a drug, the careful loading of a syringe in the field is not always practical. It is, therefore, conventional to provide the veterinarian with a syringe capable of adjustment of the dosage delivered from that syringe. These syringes are normally disposable syringes, accordingly, the veterinarian can select the proper dose for an individual animal, rapidly set the syringe for delivering only that dose, inject the animal, and dispose of the syringe with the remaining drug content therein. Alternatively, when a drug is to be administered to a large number of animals, multiple doses for a number of animals may be contained in a single syringe. The veterinarian selects the proper dosage for each animal, rapidly sets that dosage on the syringe and serially injects the animals with the proper dosage.

Since a large number of animals are often treated in a short period of time, it is most important that the adjustable syringe be capable of rapid adjustment for dosage delivered can be accurate in the dosage. Further, since these syringes are normally disposable, it is imperative that they are of such construction that is inexpensive to manufacture. Further, it is conventional to supply the syringes and drugs as a total package from the manufacturer. Therefore, the adjustable syringes must be capable of delivering dosages of varying amounts, consistent with the weight of the animal, and the increment of dosage with which the syringe may be set is relatively small.

U.S. Pat. No. 4,275,729 describes an adjustable dosage syringe wherein the syringe plunger has sets of multiple closely spaced indentations along the length of the plunger, and a dosage selection ring disposed around the plunger. The inside circumference of the dosage selection ring has protuberances, which are registrable with and receivable in one of the indentations of the set of indentations as follows. When one protuberance is received in an indentation of the first set of indentations, the other protuberance is also received in the second set of indentations. According to this invention, the desired amount of the syringe content is discharged when the plunger is engaged by the plunger-receiving end of the barrel, which is at the opposite end of the barrel.

The above patent also describes a number of art-related patented syringes. U.S. Pat. No. 3,563,240 provides a syringe with a plunger having peripheral thread thereon, and a cooperating threaded nut. By threading the nut up and down of the syringe plunger, adjustable dosage of the drug contained in the syringe may be delivered by way of the nut limiting the depression of the plunger into the syringe barrel. However, manually threading the nut up and down the plunger is relatively time-consuming, particularly when the dosage requirement from animal to animal varies considerably and the threading of the nut must be accurately performed in order to ensure that the correct dosage is given. Manufacture of such a syringe is also expensive, since it requires manual manipulation to thread the nut on the plunger during the assembling process.

Efforts have been made in the art to overcome such disadvantages, notable among which is the known "split-ring" syringe wherein the "nut" is releaseably hinged about the circumference thereof. Whereby, the nut can be opened, manually slid to the portion of the plunger desired for the appropriate dose, closed on the threads, and the appropriate dose discharged from the syringe. However, here again, this requires manual opening and closing of the hinged "nut" and can be time-consuming for the reasons expressed above.

Older approaches in the art avoided some of the problems discussed above by providing a plunger with various types of replaceable stop means, e.g., pins, clips and the like, but these approaches were too cumbersome for field use. Another approach in the older art was that of providing indentations in a ring disposed about the plunger whereby the indentations would allow the ring to be lifted and, moved along the plunger to discrete recesses in the legs of the plunger. The ring could be dropped into and set the dosage discharged by the plunger. U.S. Pat. No. 2,856,925 is representative thereof. This older approach, while being relatively rapid to operate, suffered from the disadvantages that the dosage was fixed by the size of the recesses in the legs of the plunger. Consequently, the necessary clearance in the recesses for allowing the ring to drop therein could not accurately set the dosage discharged from the syringe.

Accordingly, while the advances in the art have improved the accuracy of the dosage which can be delivered, i.e., by virtue of the threaded nut arrangement and the like, these advances have been accompanied by less convenient and rapid use of the syringes. It would, therefore, be of considerable advantage in the art to provide an adjustable dose syringe which can not only be rapidly changed to set the dosage delivered but can very accurately set that dosage and provide for very small increments of dosage adjustment.

BRIEF DESCRIPTION OF THE DRAWINGS

FIG. 2 shows a subassembly of the ring disposed on the plunger, and a subassembly of the barrel with the seal inserted therein.

FIG. 3 is an elevated view of the syringe with the plunger engaging the seal and with the ring in a fully collapsed position indicating that a selected dose had been dispensed.

FIG. 4 is a view similar to FIG. 3 showing the plunger engaged with the seal and with the ring rotated counter-clockwise to a selected dosage setting.

FIG. 5 is a view similar to FIG. 3 showing the plunger in a fully collapsed position dispensing the selected dosage.

FIG. 6 is a view similar to FIG. 3 showing the plunger engaged with the seal and with the ring at a selected dosage setting.

FIG. 7 is a view similar to FIG. 6 showing the plunger in a fully collapsed position dispensing the selected dosage.

SUMMARY OF THE INVENTION

Figure 1:
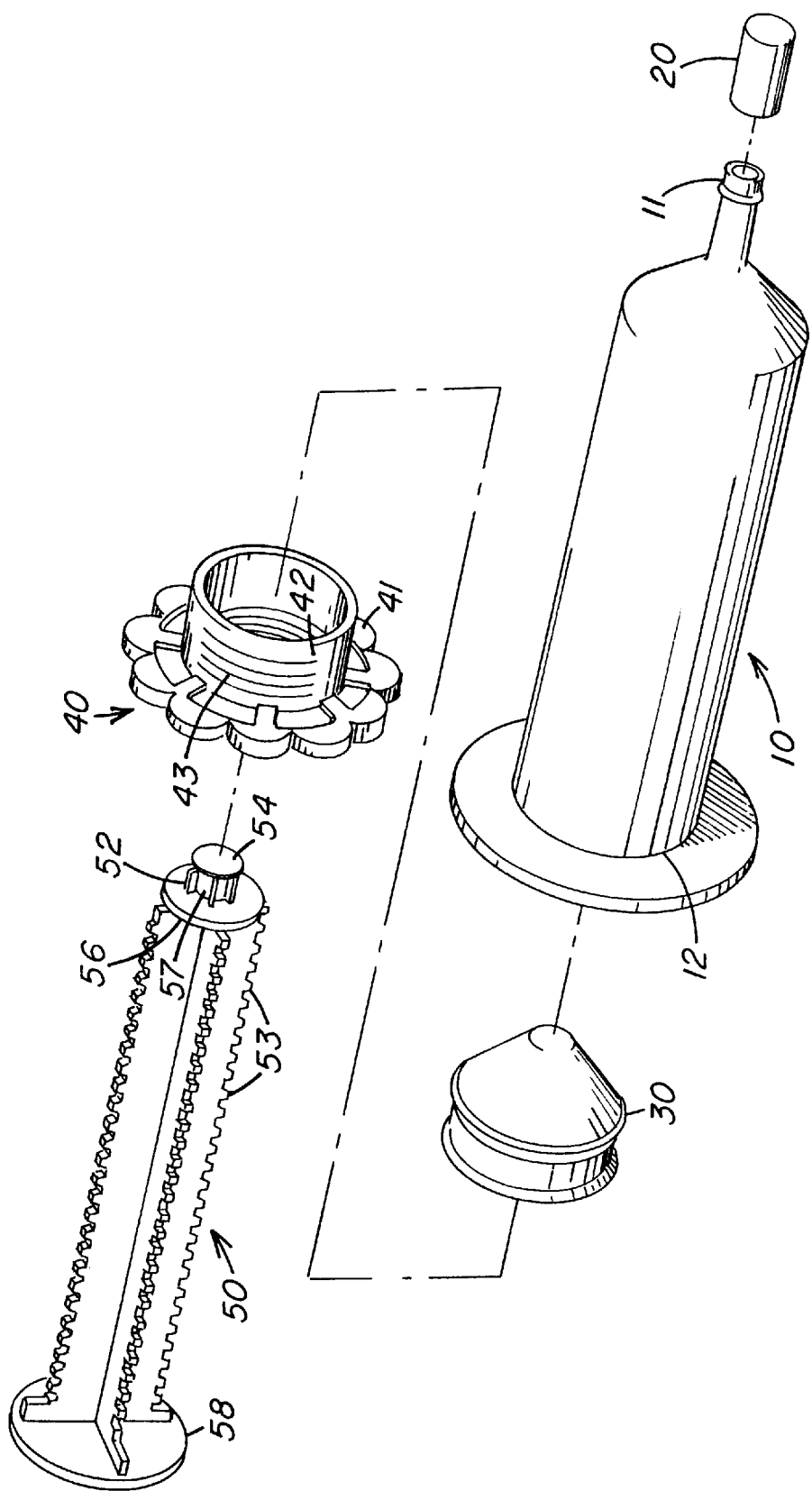
FIG. 1 is an exploded view of the syringe of the present invention, showing a preferred embodiment thereof with the centerline showing how the components can be assembled.
Figure 8:
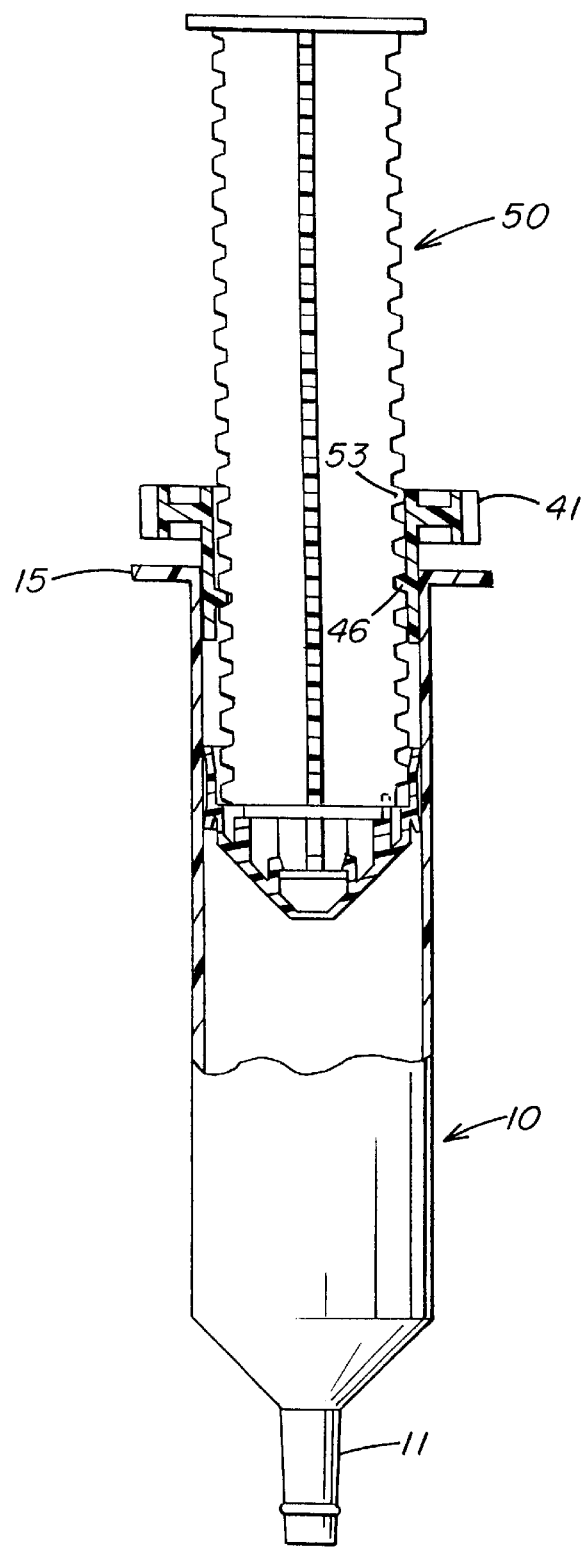
FIG. 8 is an elevated view of the syringe showing a section of the barrel in a squeegee contact with the seal, and a slight clearance from the plunger.
Figure 9:
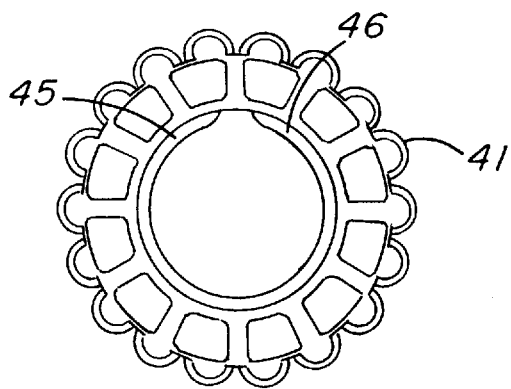
FIG. 9 is a top view of the ring.
Figure 10:
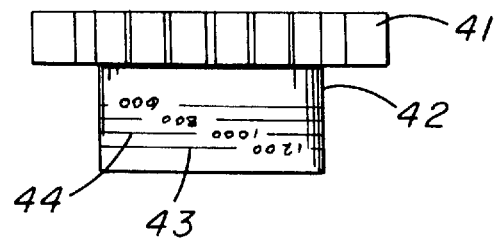
FIG. 10 is a side view of the ring showing calibrations on the sleeve.
Figure 11:
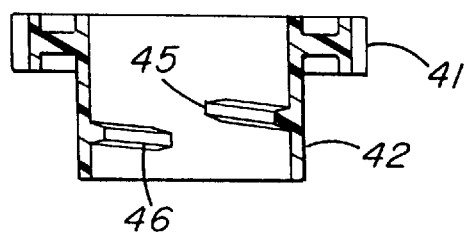
FIG. 11 is a sectional view of the ring showing the thread therein.
Figure 12:
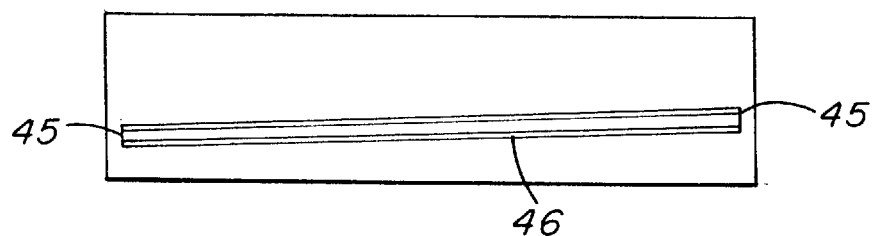
FIG. 12 is an ortho graphic spread of FIG. 11.

The present invention encompasses a self-zeroing dosage syringe comprising a syringe barrel, a plunger and dosage selection ring. The barrel has an internal length and diameter, which form a volume sufficient to contain multiple dosages of a fluid. The barrel, also, has a discharge end at one end of its length, a plunger-receiving end at the opposite end. To keep the contents of the syringe from leaking and to bear the pressure applied to discharge the contents, the sealing means is disposed over the contents. The seal can be of a shape that would engage the means for exerting pressure to discharge the contents of the barrel. Used as a means for exerting pressure in order to discharge the contents of the barrel is a plunger. The plunger is movably disposed within the barrel, has a length greater than the length of the barrel, and further has at a set of multiple closely spaced indentations disposed along the length thereof. The plunger end that is disposed inside the barrel (distal end) is of a shape that enables it to exert pressure against the content of the barrel to discharge the content. Preferably the shape of the plunger end is such as would engage a counter-part shape formed in the seal disposed against the contents of the barrel.

A dosage selection ring is movably and rotatably disposed around the plunger and at least partly inside the circumference of the barrel. The syringe is characterized in that the dosage selection ring has a sleeve movably disposed inside the barrel, and further has calibrations on its sleeve for setting the desired dosage by turning the ring until the calibration for a desired dose is reached. In the present embodiment of the invention, as the ring is turned counter-clockwise to set the desired dose, a thread in its internal circumference is received in indentations on the plunger in order to form a positive lock between them. The ring and the plunger cooperatively engage each other by means that allow the ring and the plunger to be moved together. The ring moves until it (its flange) dead-ends against the syringe barrel (flange), preventing any forward movement of the ring or plunger. As would be realized, this is the same point reached when a required dose is given. Therefore, with each given dosage, the syringe is reset at zero, thus, defining the syringe as being self-zeroing. The distance traveled by the plunger relative to syringe's internal diameter determines the amount of the content of the syringe that is discharged. When not in use, the discharge end of the barrel can be closed by means of a removable plug or cap.

The present invention is advantaged over the prior art syringes, which are less accurate in that the zero point of the prior art syringes is predetermined but unfixed. Therefore, there is certain degree of inaccuracy because the fill volume varies. Fill volume variation affects the volume of product expelled from the syringes and can therefore lead to overdosing or under-dosing. Fill volume would vary when the plunger is moved to expel trapped air from the content of the syringe.

The invention is further advantaged by the proximity of the calibrations on the sleeve of the dosage selection ring, as opposed to calibrations that are distal, which allows for more accurate dosing.

DETAILED DESCRIPTION OF THE INVENTION

The invention can be further understood by reference to the drawings. FIG. 1 shows an exploded view of a preferred embodiment of the present invention. Thus, the syringe is composed of a barrel 10 having an internal length L and an internal diameter D. The volume formed by the dimensions L and D are sufficient to contain multiple dosages of a liquid, e.g., drug, disposed in the syringe. The barrel has a discharge end 11 which, in the present embodiment of the invention, is at the conically shaped and extended end of the barrel, and a plunger-receiving end 12, at the opposite end of the barrel length. In the present embodiment of the invention, the plunger-receiving end of the barrel is shaped to form a flange 12 receiving end.

The plunger 50 as shown in FIG. 1, generally, has a length greater than the length of the barrel. The plunger has a means for engaging the dosage selection ring comprising indentations disposed along the length of the plunger. Preferably the plunger has thereon at least two sets of indentations identified as 53 in FIG. 1. The specific shape of indentations is not narrowly critical. However, the cross-sectional configuration may be square, rectangular, oval and the like, and this only necessitates that protuberances in the ring have a similar configuration, in order that the required engagement therebetween may be achieved. Preferably the indentations are angled inwards to enable the thread of the ring to move smoothly along the plunger. The distal end of the plunger (inside the barrel) is shaped to be affixed to the seal, and to apply sufficient pressure to the seal in order to move it to discharge the contents of the barrel. To affix to the seal, the plunger is equipped with a member, which contacts the seal in any convenient manner for the purpose of affixation and/or exerting pressure when the plunger is depressed. In the present embodiment of the invention, the plunger end, preferably the tip is shaped or equipped with a first plate 54 as shown in FIG. 1. Thus the plunger can be detached from the seal by exerting sufficient retracting force thereon. A second plate 56 as shown in FIG. 1, having a diameter greater than the diameter of the first place can be disposed above the first plate to provide a means for exerting pressure on the seal. The outside end of the plunger is capped with a thumb pad 58.

Figure 13:
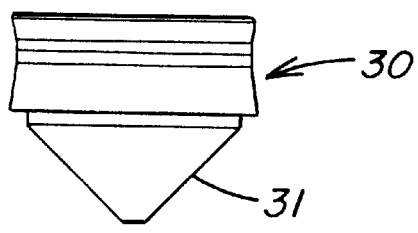
FIG. 13 is an outside elevated view of the seal.
Figure 14:
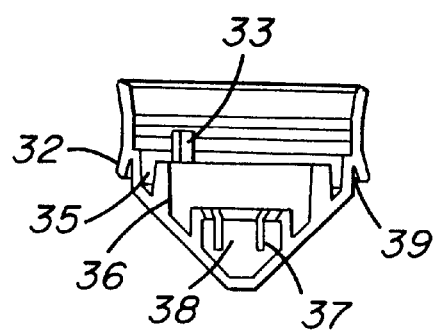
FIG. 14 is a sectional view of the seal.
Figure 15:
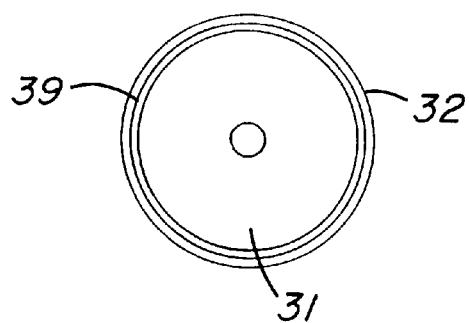
FIG. 15 is a bottom view of the seal.
Figure 16:
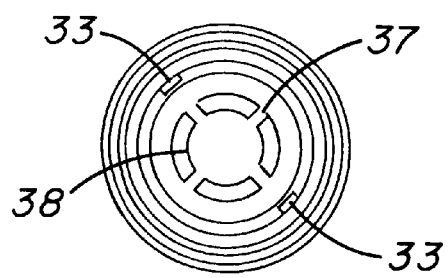
FIG. 16 is a top view of the seal.

A sealing means (seal) is disposed across the contents of the barrel to prevent the content from leaking and/or to bear pressure applied to move the seal to discharge the content. In the present embodiment of the invention, the seal 30 as shown in FIG. 13 is in frictional contact with the inside circumference of the barrel. To aid in establishing the frictional contact, the seal wall extending above the conical section 31 in FIG. 13 (upper section) is flanged, thus creating a spacing 39 as represented in FIG. 14. The seal is of hollowed shape, which receives the plunger and bears exerted pressure by the plunger to discharge the contents of the barrel. To receive the plunger, the seal comprises a first tubular housing extending from the inner wall of the conical section of the seal 31 as shown in FIG. 13. Preferably first tubular housing 38 as shown in FIG. 14 is in the form of a snap-fitting assembly wherein the wall 37 of the housing is discontinuous and yields to receive the plunger and close thereon to secure it. In the present embodiment of the invention, the first housing releasably receives the neck of the plunger 57 as shown in FIG. 1. The seal has a second tubular housing 36 as shown in FIG. 14 having a larger diameter than the first housing, and also extending from inside wall of the conical section 31 as shown in FIG. 13. The rim of the second housing abuts the plate 56 of the inserted plunger, and can thus bear applied pressure by the plunger. Preferably, there is disposed on the rim a protuberance 33 that limit plunger rotation in the housing. In the present embodiment of the invention, two protuberances are disposed on the rim of the housing. The rotation is limited when the side of plunger abuts the protuberance. To aid in receiving the plunger into the seal, the upper section of the seal is in the form a ridge along the circumference of the seal. The ridge extends sufficiently to contact the sides of the plunger as it is being inserted into the seal and thus guides the plunger into the housing of the seal. The ridged members of the seal are sectionally represented in FIG. 14 as parallel lines traversing the upper section of the seal. The ridged members are further represented from the top view in FIG. 16 as concentric circles between the circle depicting the rim of the outermost housing and the inside circumference of the upper section of the seal. It is a distinct feature of the invention that the plunger can be removed from the syringe and reused with another syringe barrel wherein the contents are sealed with the seal as described herein.

As can be seen in FIG. 2, the dosage selection ring 41 has a sleeve 42, disposed over the plunger (indentation) and partly inside the barrel. Preferably, the outside circumference of the ring and the inside circumference of the barrel have a slight clearance between them. The sleeve also has calibrations 43 marked thereon for setting the desired dosage. The dosage selection ring also has a means that cooperatively engages the plunger. The ring cooperating means comprises a protuberance disposed along the inside circumference of the ring, which configuration is suitable for being in register with the plunger means for making the engagement. Illustratively, the protuberance is received in an individual indentation 53 disposed on plunger 50 as shown in FIG. 1. In the present embodiment of the invention, the protuberance is in the form of a thread disposed along the inside circumference and having open and offset ends 45 and 46 that allow the thread to engage the indentations on the plunger. The protuberances are so disposed that when one of the protuberances is received in the first set of indentations, the other protuberance is received in the other set of indentations. The protuberance can be brought into register with the indentations by rotating the ring about the axis of the plunger. The specific shape of protuberances is not narrowly critical. However, the cross-sectional configuration may be square, oval and the like, and this only necessitates that the indentations have a similar configuration, in order that the required engagement between them may be achieved.

It is a distinct feature of the invention that the calibrations are on the outside to the dosage ring. Because of this, and because the dosage selection ring is only slightly smaller in diameter than the inside of the syringe barrel, the dosage is much more accurately dispensed. By rotating the ring counterclockwise, the dosage selection ring slideably moves longitudinally along the length of the plunger to indicate the desired dosage.

The dosage can be selected by sight through aligning the calibration to the edge of the syringe barrel. Preferably, the dosage is selected by establishing a line of sight and setting the ring from that line. In instances in which the line is not perfectly perpendicular, the dose will not be accurate. These are very close, so there is minimal possibility for error. In contrast, traditional syringes have long distances between the calibrations and syringe barrel. More unfavorable still, in the traditional syringes, the calibrations are on the horizontal surface of the plunger. Once the calibration has been set at the desired dosage, the ring is retained in a positive lock with the plunger.

While a seal can be disposed between the sleeve and the barrel, one can employ the syringe without a seal because the outside diameter of the sleeve is only slightly larger than the inside diameter of the barrel. To discharge the contents of the barrel, the ring and/or the plunger can be slid until the ring once it comes into contact with the barrel. Thus, the desired dosage of material is expelled out of the discharge end of the barrel. The amount of material delivered by the syringe is determined by the distance the plunger travels, relative to the syringe's diameter. Thus, the volume is equal to the distance of travel multiplied by a cross-sectional area.

In manufacturing the syringe, any convenient material or means can be employed. Preferably, plastic materials can be molded to make various parts of the syringe. Alternatively, other materials such as glass, metal and combinations thereof may be used.if desired. The syringe can be inexpensively manufactured by making the components thereof, and assembling them by simply sliding the ring onto the plunger from the opposite end of the thumb pad followed by inserting the plunger into the barrel which has been filled with the contents. Alternatively, the thumb pad may be removable, by means well known in the art, for slipping ring 40 onto the plunger.

Generally, the syringes of this nature can be of a volume that would contain the required amount material to be administered. Typically, the syringes will have total volumes of as little as 3 cc's up to 300 cc's, but volumes between 20 and 150 cc's are more usual. A multiple dose syringe of approximately 30 cc's has been found to be particularly useful, since it may be used for administering a drug of usual dosages of 1 to 5 cc's to a number of animals.

The syringe may be filled by any convenient means preferably by conventional automatic filling machines. Typically the barrel is filled directly from the plunger-receiving end. After filing with the desired amount of material, the seal is placed against the filled end that is proximal to the plunger-receiving end. The seal is placed in such a manner as would allow its outside circumference to be in a sealable and movable contact with the inside circumference of the barrel. Another means of filling the syringe comprising placing in the plunger a cartridge or bag containing the material that is to be discharged from the barrel. With an alternative such as this the sealing mean for the contents of the barrel and plunger would be such that would allow effective pressure to be applied to discharge the material.

The syringe is well suited to dispensing materials in predetermined amounts. Illustratively the syringe can used in administering materials to animals by disposing the opening at the end of the syringe in a position to expel the material in the animal's mouth, and depressing the thumb tab until the ring comes in contact with the barrel of the syringe. The syringe particularly suited to administering materials is in a paste form.

Yet another distinct feature of the invention is that the plunger with the dosage selection ring can be retracted from one barrel and used in combination with the dosage selection ring in another barrel.

While the invention has been described in reference to the preferred embodiments of the invention, modifications thereof will be quite apparent to those skilled in the art, and it is intended that the invention embrace those apparent modifications. Thus, the invention extends to the spirit and scope of the annexed claims.

What is claimed:

1. A self-zeroing dosage syringe comprising:
   (a) a syringe barrel with an internal length and diameter which forms a volume sufficient to contain a required dosage of a fluid, a discharge end at one end of the barrel length, a plunger receiving end at the opposite end of the barrel length,
   (b) said plunger is movably disposed within the barrel and has a length greater than the length of the barrel, and further has a set of multiple closely spaced indentations disposed along the length thereof, and
   (c) a movable dosage selection ring which is disposed around the plunger and rotatable about the longitudinal axis of the plunger; characterized in that the dosage selection ring has
      (1) a sleeve disposed inside the barrel,
      (2) a calibration on the sleeve thereof for setting the desired dosage by turning the ring until the calibration for a desired dose is reached,
      (3) a means for engaging the ring with the plunger allowing it to be moved cooperatively with the plunger until the ring dead ends against the syringe barrel thereby releasing the desired dosage.

2. The syringe of claim 1 wherein the ring is moved by means of protuberances disposed along the plunger.

3. The syringe of claim 2 wherein the movable means is a thread disposed on the inside circumference of the ring.

4. The syringe of claim 1 wherein the ring is rotated counter-clockwise until the calibration for the desired dosage is reached.

5. The syringe of claim 1 wherein the means for engaging the ring with the plunger is a lock provided by the threads of the ring with the indentation of the plunger.

6. The syringe of claim 1 which self-zeroes as the dosage ring comes into contact with the barrel of the syringe.

7. A kit comprising the dosage syringe of claim 1 and a composition of ponazuril.

8. The kit of claim 7, wherein the composition of ponazuril is in a paste form.

9. A method of administering materials to animals by disposing the opening at the end of the syringe in a position to expel the material in the animal's mouth, and depressing the dosage ring until it comes in contact with the barrel of the syringe.

10. The method of claim 9 wherein the material is in a paste form.

11. The method of claim 10 wherein the material is a composition of ponazuril.

* * * * *